United States Patent

Reginiér et al.

[11] Patent Number: 4,492,696
[45] Date of Patent: Jan. 8, 1985

[54] PIPERAZINE AND HOMOPIPERAZINE COMPOUNDS

[75] Inventors: Gilbert Reginiér, Chatenay-Malabry; Michel Laubíe, Vaucresson; Jacques Duhault, Croissy sur Seine, all of France

[73] Assignee: ADIR, Neuilly-sur-Seine, France

[21] Appl. No.: 466,603

[22] Filed: Feb. 15, 1983

[30] Foreign Application Priority Data

Feb. 17, 1982 [FR] France ................. 82 02555

[51] Int. Cl.³ ............. A61K 31/53; C07D 403/14; C07D 409/14; C07D 405/14
[52] U.S. Cl. ................. 424/249; 260/243.3; 544/198
[58] Field of Search ............ 544/198; 260/243.3; 424/249

[56] References Cited

U.S. PATENT DOCUMENTS 3,580,912  5/1971  Heimberger et al. ............. 544/198
3,647,794  3/1972  Regnier et al. ................. 544/198
4,087,609  5/1978  Smith et al. .................... 544/197

Primary Examiner—John M. Ford
Attorney, Agent, or Firm—Gordon W. Hueschen

[57] ABSTRACT

Piperazine and homopiperazine compounds of the formula:

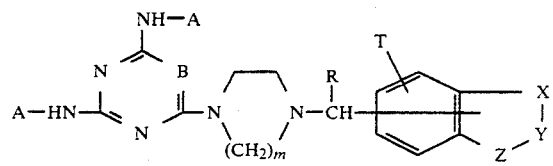

in which:
A is a hydrocarbon radical from $C_3$ to $C_5$, in a straight or branched chain, which may contain one or two double bonds, and optionally substituted by one or more OH;
B is CH or a nitrogen atom;
m is 2 or 3;
X—Y— represents —CH=CH— $(CR'R'')_n$— in which n is zero or 1, and R' and R" are hydrogen or methyl;
Z is oxygen or sulfur,
R is hydrogen, alkyl from $C_1$ to $C_5$, cycloalkyl from $C_3$ to $C_7$, or phenyl optionally substituted by fluorine, chlorine or alkyl from $C_1$ to $C_5$, and
T is hydrogen, fluorine, chlorine or alkyl from $C_1$ to $C_5$.

These compounds and physiologically tolerable acid addition salts thereof may be used as medicines especially in the treatment of all kinds of tissular hypoxy.

4 Claims, No Drawings

PIPERAZINE AND HOMOPIPERAZINE COMPOUNDS

The present invention provides piperazine and homopiperazine compounds of the formula:

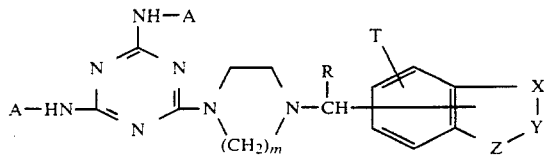

in which:

A is selected from the group consisting of hydrocarbon radicals containing from 3 to 5 carbon atoms, in straight and branched chain, these radicals containing one and two double bonds and substituted by one and two hydroxy radicals;

B is selected from the group consisting of —CH— and a nitrogen atom;

m is an integer selected from the group consisting of 2 and 3;

—X—Y— represents a group of the formula:

—CH=CH—(CR'R")$_n$— in which n is selected from the group consisting of 0 and 1 and R' and R" which are the same or different are each selected from the group consisting of a hydrogen atom and a methyl radical;

Z is selected from the group consisting of an oxygen and a sulfur atom;

R is selected from the group consisting of a hydrogen atom, an alkyl radical having from 1 to 5 carbon atoms, a cycloalkyl radical having from 3 to 1 carbon atoms, an unsubstituted phenyl radical and a phenyl radical mono- and poly-substituted by a substituent selected from the group consisting of fluorine and chlorine atoms and alkyl radicals having from 1 to 5 carbon atoms inclusive;

T is selected from the group, consisting of a hydrogen atom, a fluorine atom, a chlorine atom and alkyl radicals containing from 1 to 5 carbon atoms inclusive, and the group:

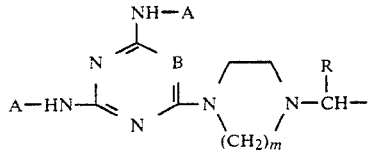

is bonded to either one of the cycles forming the group:

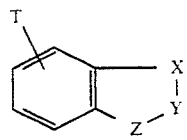

in the formula I.

The present invention further provides a process for preparing the compounds of the general formula I which comprises condensing:

either a halo compound of the general formula II

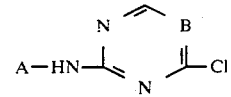

in which A and B have the meanings previously given, with a N-monosubstituted piperazine of the general formula III:

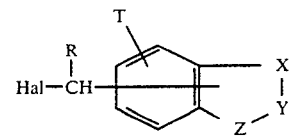

in which m, —X—Y—, Z, R and T have the above defined meanings;

or a halo compound of the general formula IV:

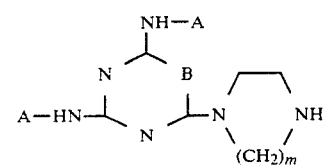

in which —X—Y—, Z, R and T have the meanings previously defined and Hal represents a halogen atom such as, for example, a chlorine or a bromine atom, with a N-monosubstituted piperazine of the general formula V:

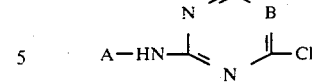

in which A, B and m have the meanings previously given.

In these two cases, such a condensation is advantageously carried out in a solvent such as, for example, an alcohol having a high boiling point such as, for example, 1-butanol or 1-pentanol, or an aliphatic amide such as, for example, dimethylformamide or dimethyl acetamide, or a benzene hydrocarbon having a high boiling point such as, for example, toluene or xylene, at a temperature within the range of 120° to 150° C., in the presence of an acceptor of the hydrochloric acid formed during the reaction. As acceptors, there may be mentioned, for example, for the condensation of compounds II and III: alkali metal salts of carbonic acid such as, for example, sodium or potassium carbonates, triethylamine and an excess of the N-monosubstituted piperazine of the formula III used in the condensation, and for the condensation of compounds IV and V: triethylamine or an excess of the N-monosubstituted piperazine of the formula V used in the condensation.

The present invention also provides a process for preparing the compounds of the general formula I which comprises:

condensing a halo compound of the general formula VI:

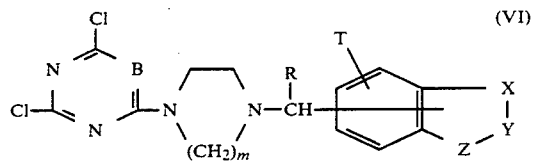

in which A, B, m, R, —X—Y—, Z and T have the meanings previously defined;

with a primary amine of the general formula VII:

A—NH$_2$   (VII)

in which A has the meaning previously defined.

Such a condensation is advantageously carried out in a solvent selected from the alcohols having a high boiling point such as, for example, dimethylformamide or dimethylacetamide. The condensation is suitably performed in an autoclave, at a temperature within the range of from 120° to 150° C., in the presence of an acceptor of the hydrochloric acid formed during the reaction. This acceptor may be triethylamine or an excess of the primary amine VII used in the condensation.

The present invention also provides the salts of the so-obtained new compounds with suitable acids. As acids which may be used there may be mentioned, for example, in the mineral series: hydrochloric, hydrobromic, sulfuric and phosphoric acids, and in the organic series: acetic, propionic, maleic, fumaric, tartaric, citric, oxalic, benzoic, methanesulfonic and isethionic acids.

The compounds of the general formula I may be purified by physical methods such as, for example, crystallisation or chromatography or by chemical methods, such as, for example, formation of addition salts with acids, crystallisation of these salts and decomposition thereof by alkaline agents.

The starting materials used in the above processes are either known products or compounds prepared according to methods described in the literature for preparing similar compounds, as mentioned in the following Examples.

For example, the products of the general formula II were prepared according to a process analogous to the one described in the French Patent No. 1,507,062. Furthermore, the compounds of the general formula II in which A represents an allyl radical are described in the British Pat. No. 1,342,828. The starting materials of the general formula V in which B is a nitrogen atom and A represents an allyl, crotyl or dimethyl allyl radical, were prepared according to the process described by R. BALTZY et als., J. Org. Chem. 24, 459 (1959). They were also described in the French Pat. No. 2,019,646.

The starting materials of the formula:

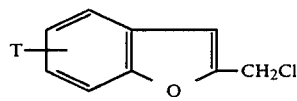

in which T represents an hydrogen or fluorine atom, were prepared by analogy with the method of W. ANDERSON et als., J. Pharm. Sci. 69, 232 (1980).

The starting materials of the formula:

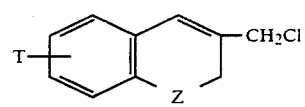

in which Z represents an oxygen or a sulfur atom were prepared starting from the corresponding 3-formyl chromenes or thio-chromenes, according to C. DEBOER, J. Org. Chem. 39, 2426 (1974), reduction of these compounds with NaBH$_4$ and chlorination with SOCl$_2$.

The starting materials of the formula:

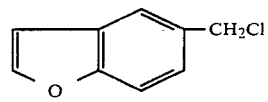

were prepared by chlorination of the corresponding alcohols themselves prepared by reduction with LiAlH$_4$ of the corresponding acids obtained according to F. DURO et al., Ann. Chim. Rome 53, 1582 (1963).

The starting materials of the formula:

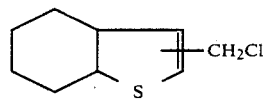

were prepared according to F. BLICKE et al., Am. Soc. 70, 3768 (1948) and Am. Soc. 71, 2856 (1949).

The starting materials of the formula:

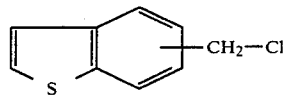

were prepared according to Y. MATSUKI, C.A. 65, 15.301 g (1966).

The compounds of the general formula I and physiologically tolerable addition salts thereof possess valuable pharmacological and therapeutic properties. In particular, they promote the uptake of oxygen. They may be used as medicines, especially in the treatment of all kinds of tissular hypoxy.

Their toxicity is low, and the LD$_{50}$, determined in mice varies from 100 to more than 200 mg/kg by intraperitoneal route.

The activity of the compounds of the present invention on the pressure of oxygen (PO$_2$) was studied in the dog anaesthetised with pentobarital. Samples of blood were periodically taken 2, 5, 15, 45 and 75 minutes after administration of the compounds to be tested; they are used for the determination of pH, PO$_2$ and PCO$_2$.

The pressure of oxygen (PO$_2$) was measured on an apparatus called Radiometer BMS$_3$. The reading of PO$_2$ was made on this apparatus previously guaged with known values, by means of an electrode in platinum or Clark electrode.

The compounds were administered in the dog by intravenous route at a dose of 1 mg/kg and the determination of the percentage increase in the level of oxygen in the arterial blood shows that this percentage can, according to the compounds, reach 35.4% 15 minutes after administration of the compound, and 31.4% 75 minutes after administration of the compound.

The present invention also provides pharmaceutical compositions containing as active principle a compound of the general formula I or a physiologically tolerable salt thereof, in admixture or conjunction with a suitable pharmaceutical carrier.

The pharmaceutical compositions thus obtained are advantageously in unit dosage form and may contain from 20 to 100 mg of active ingredient. They may be in the form of tablets, dragees, capsules, suppositories, injectable or drinkable solutions, and administered by oral, rectal or parental routes at doses within the range of 20 to 100 mg of active ingredient, once to twice a day.

The following examples illustrate the invention:

EXAMPLE 1

1-(4,6-bis allylamino s.triazin-2-yl)-4-(benzofuran-2-yl methyl)piperazine.

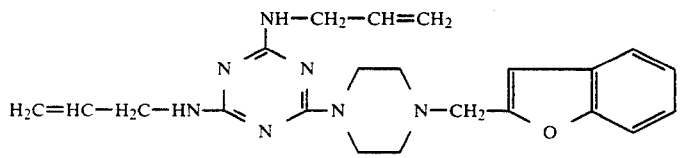

First method

A solution of 13.8 g of 1-(4,6-bis allylamino s. triazin-2-yl)piperazine, M.P. (Kofler): 100° C., and 2-chloromethyl benzofuran (B.P./0.5 mmHg: 82°–85° C.) in the presence of 7.6 ml of triethylamine in 200 ml of anhydrous toluene containing 10 ml of dimethylformamide, was refluxed for 3 hours. Upon completion of the reaction, the organic solution was washed with 100 ml of water, then the base was extracted with twice 75 ml of a 2N CH$_3$SO$_3$H solution.

The solution was then alkalized with an excess of K$_2$CO$_3$ and the product was extracted with benzene. The benzene solution was evaporated; there were obtained 22 g of an oily product which was dissolved in 100 ml of anhydrous ethanol. The solution was filtered on carbon black and acidified with 50 ml of a 2N solution of HCl in ether. 17.8 g of 1-(4,6-bis allylamino s. triazin-2-yl)-4-(benzofuran-2-yl methyl)piperazine dihydrochloride cristallised in the form of white crystals melting (Kofler) at: 230° C.

Second method

A solution of 10.3 g of 1-(benzofuran-2-yl methyl)piperazine (B.P./0.015 mmHg: 125°–128° C.) and 11.3 g of 4,6-bis allylamino-2-chloro s.triazine, M.P. (Kofler): 204° C., in the presence of 6.9 g of K$_2$CO$_3$ in 200 ml of butanol was refluxed for 5 hours. Upon completion of the reaction, the salt was filtered off and the filtrate was evaporated under reduced pressure. The residue was dissolved in benzene. The benzene solution was twice extracted with 75 ml of a 2N monomethane sulfonic acid solution. There were obtained 19 g of crude base which was converted into the corresponding dihydrochloride, as described in the first method. There were finally obtained 16 g of 1-(4,6-bis allylamino s. triazin-2-yl)-4-(benzofuran-2-yl methyl)piperazine dihydrochloride, melting (Kofler) at 229°–230° C.

Third method

A solution of 18.2 g of 1-(4,6-dichloro s. triazine-2-yl)-4-(benzofuran-2-yl methyl)piperazine and 150 g of allylamine in 500 ml of dimethylformamide was heated at 145° C. for 8 hours. Upon the completion of the reaction, the solvent was evaporated under reduced pressure. The pasty residue was dissolved in benzene and washed several times with water. The solvent was evaporated and the oily residue (20 g) was dissolved in 100 ml of ethanol, then converted into dihydrochloride as mentioned in the first method. There were finally obtained 17.5 g of 1-(4,6-bis allylamino s. triazin-2-yl)-4-(benzofuran-2-yl methyl)piperazine dihydrochloride, melting (Kofler) at 230° C.

The starting 1-(4,6-dichloro s. triazin-2-yl)-4-(benzofuran-2-yl methyl)piperazine was prepared by reaction of cyanuryl chloride with 1-(benzofuran-2-yl methyl)piperazine, in methylethyl ketone, in the presence of NaHCO$_3$.

EXAMPLES 2 TO 18

The following compounds were prepared according to the methods given in Example 1:

(2) 1-(4,6-bis allylamino s.triazin-2-yl)-4-(3-chromene-3-yl methyl)piperazine, M.P. (Kofler) of its methane sulfonate: 154° C. (acetonitrile).

(3) 1-(4,6-bis allylamino s.triazin-2-yl)-4-(benzothien-5-yl methyl)piperazine, M.P. (Kofler): 108° C. (acetonitrile).

(4) 1-(4,6-bis allylamino s.triazin-2-yl)-4-(benzofuran-5-yl methyl)piperazine, M.P. (Kofler) of its difumarate: 200° C. (anhydrous ethanol).

(5) 1-(4,6-bis allylamino s.triazin-2-yl)-4-(5-fluorobenzofuran-5-yl methyl)piperazine, M.P. (Kofler): 122° C. (actonitrile).

(6) 1-(4,6-bis allylamino s.triazin-2-yl)-4-(thio-chrom-3-ene-3-yl methyl)piperazine, M.P. (Kofler): 105° C. (acetonitrile).

(7) 1-(4,6-bis allylamino s.triazin-2-yl)-4-(5-fluorochrom-3-ene-3-yl methyl)piperazine, M.P. (Kofler): 120° C. (acetonitrile).

(8) 1-(4,6-bis allylamino s.triazin-2-yl)-4-(benzothien-2-yl methyl)piperazine, M.P. (Kofler): 108° C. (acetonitrile).

(9) 1-(4,6-bis allylamino s.triazin-2-yl)-4-(benzothien-3-yl methyl)piperazine, M.P. (Kofler) of its fumarate: 208° C. (ethanol).

(10) 1(4,6-bis allylamino s.triazin-2-yl)-4-[(benzofuran-2-yl)p. fluorophenyl methyl]piperazine, M.P. (Kofler): 160° C. (isopropranol).

(11) 1-(4,6-bis crotylamino s.triazin-2-yl)-4-(benzofuran-2-yl methyl)piperazine, M.P. (Kofler) of its difumarate: 144° C. (anhydrous ethanol).

(12) 1-(2,4-bis allylamino pyrimidin-6-yl)-4-(benzofuran-2-yl methyl)piperazine, M.P. (Kofler) of its fumarate: 184° C. (ethanol).

(13) 1-(2,4-bis allylamino pyrimidin-6-yl)-4-(chrom-3-ene-3-yl methyl)piperazine, M.P. (Kofler): 115° C. (acetonitrile).

(14) 1-(2,4-bis allylamino pyrimidin-6-yl)-4-(benzothien-5-yl methyl)piperazine, M.P. (KOFLER) of its fumarate: 205° C. (ethanol).

(15) 1-(2,4-bis allylamino pyrimidin-6-yl)-4-(benzofuran-5-yl methyl)piperazine, M.P. (Kofler) of its difumarate: 165° C. (anhydrous ethanol).

(16) 1-(2,4-bis allylamino pyrimidin-6-yl)-4-[(5-fluorobenzofuran-2-yl)methyl]piperazine, M.P. (Kofler) of its fumarate: 198° C. (anhydrous ethanol).

(17) 1-(2,4-bis allylamino pyrimidin-6-yl)-4-[(5-fluoro chrom-3-ene-3-yl)methyl]piperazine, M.P. (Kofler) of its fumarate: 228° C. (anhydrous ethanol).

(18) 1-(2,4-bis allylamino pyrimidin-6-yl)-4-(benzothien-2-yl methyl), M.P. (Kofler) of its fumarate: 222° C. (anhydrous ethanol).

We claim:

1. A compound selected from the group consisting of:
piperazine and homopiperazine compounds of the formula:

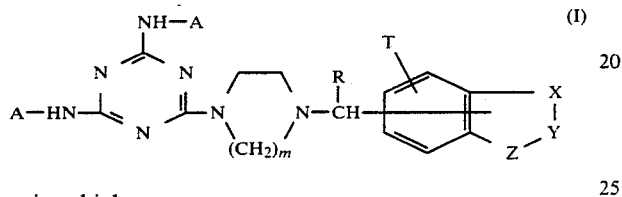 (I)

in which:

A is selected from the group consisting of hydrocarbon radicals having from 3 to 5 carbon atoms inclusive, in straight and branched chain and these radicals containing one and two double bonds and substituted by one and two hydroxy;

m is an integer selected from 2 and 3;

—X—Y— represents a group of the formula:

—CH=CH—(CR'R")$_n$— in which n is selected from the group consisting of 0 and 1, and R' and R" which are the same or different are each selected from the group consisting of hydrogen and methyl;

Z is selected from the group consisting of oxygen and sulfur;

R is selected from the group consisting of hydrogen, alkyl having from 1 to 5 carbon atoms inclusive, cycloalkyl having from 3 to 7 carbon atoms inclusive, unsubstituted phenyl and phenyl mono- and poly-substituted by a substituent selected from the group consisting of fluorine, chlorine and alkyl having from 1 to 5 carbon atoms inclusive;

T is selected from the group consisting of hydrogen, fluorine, chlorine and alkyl having from 1 to 5 carbon atoms inclusive, and the group

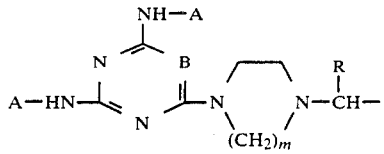

is bonded to either one of the cycles forming the group:

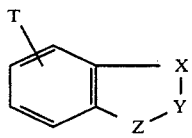

in the formula I; and physiologically tolerable addition salts thereof.

2. A compound of claim 1 which is 1-(4,6-bis allylamino s.triazin-2-yl)-4-(benzothien-5-yl methyl)piperazine.

3. A pharmaceutical composition, suitable for use in the treatment of hypoxia, containing as active ingredient a compound of claim 1, in an amount effective for such purpose, together with a suitable pharmaceutical carrier.

4. A method for treating a living animal body afflicted with a tissular hypoxy, comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,492,696
DATED : January 8, 1985
INVENTOR(S) : Gilbert Regnier, Michel Laubie and Jacques Duhault It is certified that error appears in the above-identified patent and that said Letters Patent is hereby corrected as shown below:

Title page, top of the page, left hand side under "United States Patent [19]"; "Reginier et al." should read -- Regnier et al. -- (Declaration)
Title page, [75] Inventors; "Reginier" should read -- Regnier -- (Declaration)
Col. 1, in the first formula the "N" should be changed to -- B -- as shown below:

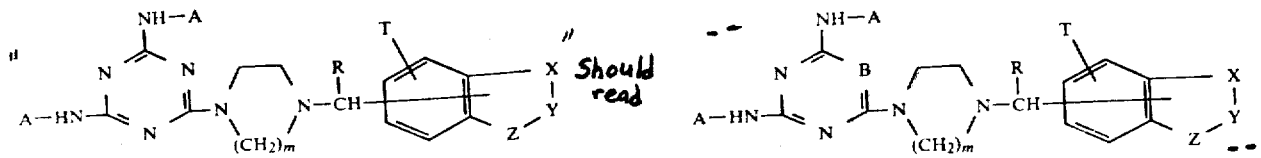

Col. 4, line 62; "guaged" should read -- gauged --
Col. 5, line 48; "cristallised" should read -- crystallised --
Col. 5, line 67; "triazine-2-" should read -- triazin-2- --
Col. 8, in the first formula the "B" should be changed to -- N -- as shown below:

Signed and Sealed this

Fifteenth Day of October 1985

[SEAL]

Attest:

Attesting Officer

DONALD J. QUIGG

Commissioner of Patents and Trademarks—Designate